United States Patent [19]

Perez

[11] Patent Number: 5,856,159
[45] Date of Patent: Jan. 5, 1999

[54] PRODUCTION OF GALACTOSYLTRANSFERASE

[75] Inventor: Carl Perez, San Diego, Calif.

[73] Assignee: Cytel Corporation, San Diego, Calif.

[21] Appl. No.: 622,753

[22] Filed: Mar. 27, 1996

[51] Int. Cl.$^6$ .......................... C12N 15/09; C12N 15/54; C12N 5/10
[52] U.S. Cl. .......................... 435/193; 435/325; 435/355; 435/70.4; 435/320.1; 536/23.2
[58] Field of Search ..................... 435/355, 193, 435/325, 70.4, 320.1; 536/23.2

[56] References Cited

U.S. PATENT DOCUMENTS

| 5,627,033 | 5/1997 | Smith et al. | 435/6 |
| 5,674,834 | 10/1997 | Theofan et al. | 514/2 |

FOREIGN PATENT DOCUMENTS

86/05807   10/1986   WIPO .

OTHER PUBLICATIONS

C.R. Bebbington et al., "High–Level Expression of a Recombinant Antibody From Myeloma Cells Using a Glutamine Synthetase Gene as an Amplifiable Selectable Marker", Biotechnology 10(2): 169–175, Feb. 92.

H. Narimatsu et al., "Cloning and Sequencing of cDNA of Bovine N–Acetylglucosamine (β1–4) Galactosyltransferase", Proc. Natl. Acad. Sci. 83:4720–4724.

S.S. Apte et al., "The Gene Structure of Tissue Inhibitor of Metalloproteinases (TIMP)–3 and Its Inhibitory Activities Define the Distinct TIMP Gene Family", J. Biol. Chem. 270(24): 14313–14318, Jun. 95.

*Primary Examiner*—Rebecca E. Prouty
*Attorney, Agent, or Firm*—Fish & Richardson P.C.

[57] ABSTRACT

A gene expression system for producing galactosyltransferase comprises an NSO cell recombinantly modified with a polynucleotide encoding galactosyltransferase or a portion thereof which catalyzes the reaction:

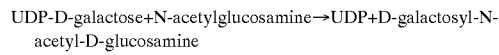

UDP-D-galactose+N-acetylglucosamine→UDP+D-galactosyl-N-acetyl-D-glucosamine

Further provided is a method for producing galactosyltransferase by culturing the gene expression system.

2 Claims, 4 Drawing Sheets

GT

ATG GCC CTC TGG ATG CGC CTC CTG CCC CTG CTG GCC CTG CTG GCC CTC
MET ALA LEU TRP MET ARG LEU LEU PRO LEU LEU ALA LEU LEU ALA LEU
Human preproinsulin leader TGG GCG CCC GCG CCC ACC CGA GCC    TTC GTT GAC TCT AGA GGA TCC
TRP ALA PRO ALA PRO THR ARG ALA    PHE VAL ASP SER ARG GLY SER
signal peptidase cleavage site ↑

CCG GGC GAG CTC CGG CTG CGA
PRO GLY GLU LEU ARG LEU ARG
⇑ Start of GT

ATG GCC CTC TGG ATG CGC CTC CTG CCC CTG CTG GCC CTG CTG GCC CTC
MET ALA LEU TRP MET ARG LEU LEU PRO LEU LEU ALA LEU LEU ALA LEU
Human preproinsulin leader TGG GCG CCC GCG CCC ACC CGA GCC    TTC GTT GAC TCT AGA GGA TCC
TRP ALA PRO ALA PRO THR ARG ALA    PHE VAL ASP SER ARG GLY SER
signal peptidase cleavage site ↑

CAA TGG GAA GAC TCC AAT TCA
GLN TRP GLU ASP SER ASN SER
⇑ Start of ST

FIG. IB

FTVII

ATG GCC CTC TGG ATG CGC CTC CTG CCC CTG CTG GCC CTG CTG GCC CTC
MET ALA LEU TRP MET ARG LEU LEU PRO LEU LEU ALA LEU LEU ALA LEU
Human preproinsulin leader TGG GCG CCC GCG CCC ACC CGA GCC    TTC GTT GAC TCT AGC CCG GCA
TRP ALA PRO ALA PRO THR ARG ALA    PHE VAL ASP SER SER PRO ALA
signal peptidase cleavage site ↑              ⇑ Start of ST

CCC CAG CCC ACG ATC ACC ATC
PRO GLN PRO THR ILE THR ILE

FIG. IC

GNT

ATG GCC CTC TGG ATG CGC CTC CTG CCC CTG CTG GCC CTG CTG GCC CTC
MET ALA LEU TRP MET ARG LEU LEU PRO LEU LEU ALA LEU LEU ALA LEU
Human preproinsulin leader TGG GCG CCC GCG CCC ACC CGA GCC    TTC GTT GAC TCT AGA CTT ACA
TRP ALA PRO ALA PRO THR ARG ALA    PHE VAL ASP SER ARG LEU THR
signal peptidase cleavage site ↑              ⇑ Start of GNT

ACA GAC TTC AGC ACC TTC AAG
THR ASP PHE SER THR PHE LYS

FIG. ID

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 114 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..114

( x i ) SEQUENCE DESCRIPTION: SEQ ID NO:1:

```
ATG  GCC  CTC  TGG  ATG  CGC  CTC  CTG  CCC  CTG  CTG  GCC  CTG  CTG  GCC  CTC        48
Met  Ala  Leu  Trp  Met  Arg  Leu  Leu  Pro  Leu  Leu  Ala  Leu  Leu  Ala  Leu
 1                    5                        10                       15

TGG  GCG  CCC  GCG  CCC  ACC  CGA  GCC  TTC  GTT  GAC  TCT  AGA  GGA  TCC  CCG        96
Trp  Ala  Pro  Ala  Pro  Thr  Arg  Ala  Phe  Val  Asp  Ser  Arg  Gly  Ser  Pro
              20                        25                       30

GGC  GAG  CTC  CGG  CTG  CGA                                                          114
Gly  Glu  Leu  Arg  Leu  Arg
           35
```

( 2 ) INFORMATION FOR SEQ ID NO:2:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Leu  Trp  Met  Arg  Leu  Leu  Pro  Leu  Leu  Ala  Leu  Leu  Ala  Leu
 1                    5                        10                       15

Trp  Ala  Pro  Ala  Pro  Thr  Arg  Ala  Phe  Val  Asp  Ser  Arg  Gly  Ser  Pro
              20                        25                       30

Gly  Glu  Leu  Arg  Leu  Arg
           35
```

( 2 ) INFORMATION FOR SEQ ID NO:3:

( i ) SEQUENCE CHARACTERISTICS:
        ( A ) LENGTH: 114 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..114

( x i ) SEQUENCE DESCRIPTION: SEQ ID NO:3:

```
ATG  GCC  CTC  TGG  ATG  CGC  CTC  CTG  CCC  CTG  CTG  GCC  CTG  CTG  GCC  CTC        48
Met  Ala  Leu  Trp  Met  Arg  Leu  Leu  Pro  Leu  Leu  Ala  Leu  Leu  Ala  Leu
 40                   45                       50

TGG  GCG  CCC  GCG  CCC  ACC  CGA  GCC  TTC  GTT  GAC  TCT  AGA  GGA  TCC  CAA        96
Trp  Ala  Pro  Ala  Pro  Thr  Arg  Ala  Phe  Val  Asp  Ser  Arg  Gly  Ser  Gln
 55                   60                       65                       70

TGG  GAA  GAC  TCC  AAT  TCA                                                          114
Trp  Glu  Asp  Ser  Asn  Ser
```

75

( 2 ) INFORMATION FOR SEQ ID NO:4:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ala Leu Trp Met Arg Leu Leu Pro Leu Leu Ala Leu Leu Ala Leu
 1               5                  10                  15
Trp Ala Pro Ala Pro Thr Arg Ala Phe Val Asp Ser Arg Gly Ser Gln
                20                  25                  30
Trp Glu Asp Ser Asn Ser
                35
```

( 2 ) INFORMATION FOR SEQ ID NO:5:

( i ) SEQUENCE CHARACTERISTICS:
        ( A ) LENGTH: 114 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..114

( x i ) SEQUENCE DESCRIPTION: SEQ ID NO:5:

```
ATG GCC CTC TGG ATG CGC CTC CTG CCC CTG CTG GCC CTG CTG GCC CTC    48
Met Ala Leu Trp Met Arg Leu Leu Pro Leu Leu Ala Leu Leu Ala Leu
 40                  45                  50

TGG GCG CCC GCG CCC ACC CGA GCC TTC GTT GAC TCT AGC CCG GCA CCC    96
Trp Ala Pro Ala Pro Thr Arg Ala Phe Val Asp Ser Ser Pro Ala Pro
 55                  60                  65                  70

CAG CCC ACG ATC ACC ATC                                            114
Gln Pro Thr Ile Thr Ile
                75
```

( 2 ) INFORMATION FOR SEQ ID NO:6:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ala Leu Trp Met Arg Leu Leu Pro Leu Leu Ala Leu Leu Ala Leu
 1               5                  10                  15
Trp Ala Pro Ala Pro Thr Arg Ala Phe Val Asp Ser Ser Pro Ala Pro
                20                  25                  30
Gln Pro Thr Ile Thr Ile
                35
```

( 2 ) INFORMATION FOR SEQ ID NO:7:

( i ) SEQUENCE CHARACTERISTICS:
        ( A ) LENGTH: 114 base pairs
        ( B ) TYPE: nucleic acid
        ( C ) STRANDEDNESS: single
        ( D ) TOPOLOGY: linear ( i x ) FEATURE:
    ( A ) NAME/KEY: CDS
    ( B ) LOCATION: 1..114

( x i ) SEQUENCE DESCRIPTION: SEQ ID NO:7:

```
ATG GCC CTC TGG ATG CGC CTC CTG CCC CTG CTG GCC CTG CTG GCC CTC        48
Met Ala Leu Trp Met Arg Leu Leu Pro Leu Leu Ala Leu Leu Ala Leu
    40                  45                  50

TGG GCG CCC GCG CCC ACC CGA GCC TTC GTT GAC TCT AGA CTT ACA ACA        96
Trp Ala Pro Ala Pro Thr Arg Ala Phe Val Asp Ser Arg Leu Thr Thr
55                  60                  65                  70

GAC TTC AGC ACC TTC AAG                                                114
Asp Phe Ser Thr Phe Lys
                75
```

( 2 ) INFORMATION FOR SEQ ID NO:8:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Ala Leu Trp Met Arg Leu Leu Pro Leu Leu Ala Leu Leu Ala Leu
1               5                   10                  15

Trp Ala Pro Ala Pro Thr Arg Ala Phe Val Asp Ser Arg Leu Thr Thr
            20                  25                  30

Asp Phe Ser Thr Phe Lys
                35
```

PRODUCTION OF GALACTOSYLTRANSFERASE

BACKGROUND OF THE INVENTION

1. Field of the Invention

This invention relates to a gene expression system for producing galactosyltransferase from a recombinantly modified myeloma cell, and to method for producing galactosyltransferase using the recombinantly modified myeloma cell.

2. Description of the Related Art

The production of biologic products from cells grown in mass cultures has a long history. Before the advent of recombinant genetic technology, the selection of cells or cell lines for production of biological products was a slow and haphazard process.

Today, recombinant genetic technology allows cells to be modified by inserting genes that encode 'foreign' proteins which are not normally produced by a host cell, creating cell lines that produce foreign proteins—antibodies, enzymes, hormones (Current Protocols in Molecular Biology, eds. Ausubel, F. M., et al. Chapter 16, 1994). However, it is not predictable whether any particular gene or host cell combination will lead to a useful level of production.

A typical technique for improving the yield of protein harvestable from recombinant mammalian cells involves stressing the cells by nutritional deprivation, temperature extremes, or other physico-chemical techniques. When stressed, the cell line's production of the desired material dramatically increases just prior to the death of the cells. A significant disadvantage of cell stress techniques is an increase in contaminants, especially proteolytic enzymes, that are released from the cells at the time of their death. The presence of these proteolytic enzymes may often damage the cloned protein as well as complicate procedures required to purify the cloned protein. While some proteins, such as monoclonal antibodies, are not subject to degradation by proteolytic enzymes, other biological material, in particular enzymes, are far more sensitive to the presence of proteolytic enzymes. Other disadvantages of the cell death approach to culture are that it requires extra labor to restart the manufacturing cell line after each batch death, requires cleansing from the culture system of proteolytic enzymes and other contaminants released from dead cells in the previous batch, and requires reinoculation of a fresh medium with concomitant waiting until the culture reaches sufficient cell density to initiate a stress-induced death. Consequently, production of cloned enzymes by the cell stress approach is not generally practical.

In view of the foregoing, there is a need for a gene expression system for producing enzymes and a method of producing enzymes which would allow continuous, longer-term scale-up production of enzymes which avoids the disadvantages of contamination from cultured host cells which are stressed to induce death and the down-time associated with the restarting of the fermentor culture.

SUMMARY OF THE INVENTION

A gene expression system is provided for producing galactosyltransferase. The gene expression system comprises a myeloma cell having the characteristics of an NSO cell which has been recombinantly modified with a polynucleotide encoding galactosyltransferase or a portion thereof which catalyzes the reaction:

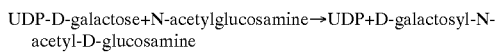

One embodiment of the invention is directed to a genetic expression system having a polynucleotide encoding UDP-D-galactose:N-acetylglucosamine β-1,4-galactosyltransferase. Included in the invention is a cell line having the accession number ATCC No. CRL-12066.

Further provided is a method for producing galactosyltransferase. The method involves the step of culturing a gene expression system which comprises a myeloma cell having the characteristics of an NSO cell which has been recombinantly modified with a polynucleotide encoding galactosyltransferase or a portion thereof which catalyzes the reaction:

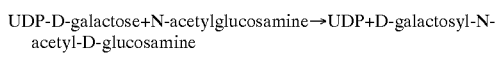

and harvesting the galactosyltransferase. A preferred embodiment of the method is directed to the use of the claimed genetic expression system which produces UDP-D-galactose:N-acetylglucosamine β-1,4-galactosyltransferase.

It is an object of the invention to provide a gene expression system for producing galactosyltransferase and a method for producing galactosyltransferase which do not require cell-stress techniques to boost galactosyltransferase production, and provide the advantage of galactosyltransferase production without substantial proteolytic damage and contamination from cell death.

A further object of the invention is to provide a gene expression system for production of galactosyltransferase and a method for producing galactosyltranserese which operates continuously for longer periods than cell stress enzyme production systems, allowing continuous harvest of enzyme; and which, upon harvesting, does not require extra labor and material for reinoculating into fresh media in sterile vessels in order to eliminate proteolytic enzymes and other contaminants.

These and many other features and attendant advantages of the present invention will become better understood by reference to the following detailed description of the invention when taken in conjunction with the Examples.

BRIEF DESCRIPTION OF THE DRAWINGS

FIGS. 1A–1D show the nucleotide sequence and amino acid sequence of the fusion junction of the human preproinsulin leader and the stem regions of (A) galactosyltransferase, (B) sialyltransferase, C) fucosyltransferase, and (D) N-acetylgalactosaminyltransferase.

DESCRIPTION OF THE PREFERRED EMBODIMENTS

Figure 2:
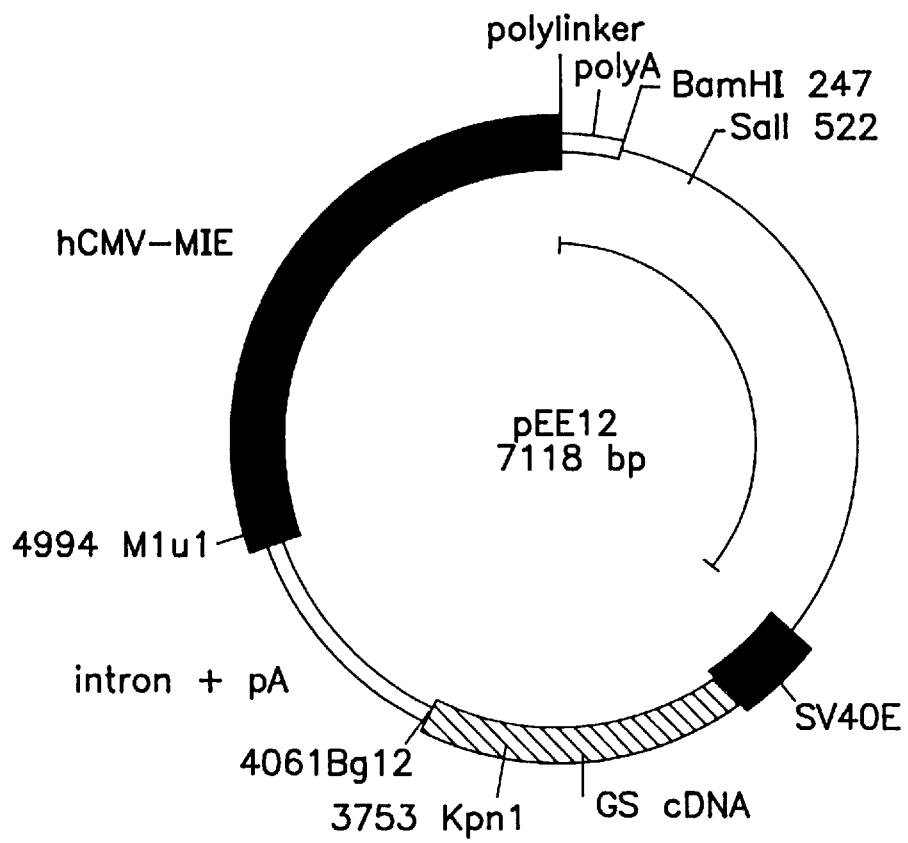
FIG. 2 is a physical map of the NSO-expression plasmid vector pEE12.

The invention provides a gene expression system for producing galactosyltransferase. The gene expression system comprises a myeloma cell which has the characteristics of an NSO cell recombinantly modified with a polynucleotide encoding galactosyltransferase or a portion thereof which catalyzes the reaction:

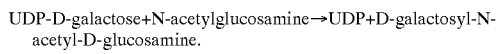

UDP-D-galactose+N-acetylglucosamine→UDP+D-galactosyl-N-acetyl-D-glucosamine.

A preferred gene expression system of the invention involves an NSO-like cell modified with a polynucleotide encoding UDP-D-galactose:N-acetylglucosamine β-1,4-galactosyltransferase or a portion thereof. An embodiment of this preferred gene expression system has been deposited in the American Type Culture Collection (ATCC), and has the accession number ATCC No. CRL 12066.

The invention also provides a method for producing galactosyltransferase, in particular, UDP-D-galactose:N-acetylglucosamine β-1,4-galactosyltransferase or a portion thereof which catalyzes the reaction:

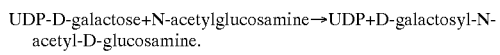

UDP-D-galactose+N-acetylglucosamine→UDP+D-galactosyl-N-acetyl-D-glucosamine.

The method involves culturing a gene expression system under conditions sufficient to produce the galactosyltransferase. The gene expresion system comprises a myeloma cell having the characteristics of an NSO cell, i.e., an NSO-like cell, which has been recombinantly modified with a polynucleotide encoding a galactosyltransferase or a portion thereof which catalyzes the reaction:

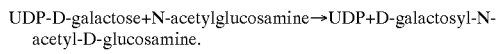

UDP-D-galactose+N-acetylglucosamine→UDP+D-galactosyl-N-acetyl-D-glucosamine.

The method is also directed to harvesting the galactosyltransferase. A further step of the method involves substantially purifying the harvested galactosyltransferase.

As used herein, the term "recombinantly modified" means introducing a polynucleotide encoding GT into a living cell or gene expression system. Usually, the polynucleotide is present in a plasmid or other vector, although modification can also occur by uptake of free GT polylnucleotide or numerous other techniques known in the art.

As used herein, the term "gene expression system" means a living mammalian cell into which a gene, whose product is to be expressed, has been introduced.

As used herein, the term "harvesting" means collecting or separating from the gene expression system the product produced by the inserted polynucleotide.

As used herein, the term "NSO-like" means a myeloma or lymphoid cell which has been derived from murine myeloma cells. NSO cells are highly transfectable and do not grow nor yield variants that grow in glutamine-free selection media.

Glycosyltransferases

Glycosyltransferases are involved in the biosynthesis of glycoprotein and glycolipid sugar chains, and are located in the membrane of the endoplasmic reticulum and the Golgi apparatus. Glycosyltransferases transfer sugar residues from an activated donor substrate, usually a nucleotide sugar, to a growing carbohydrate group. The structures of the sugar chains produced by a cell is largely determined by the specificity of the glycosyltransferase for their donor and acceptor substrates. More than 100 glycosyltransferases are estimated to be required for synthesizing known carbohydrate structures on glycoproteins and glycolipids. Most of these glycosyltransferases are involved in elaborating diverse terminal sequences (Sadler, J. E. Biology of Carbohydrates, Ginsburg, V and Robbins, P. W., eds, Vol. 2 pp. 87–131, 1984, John Wiley and Sons, New York; Beyer, T. A., et al., Adv. Enzymol. Relat. Areas Mol. Biol. 52:22–175, 1981).

These enzymes are typically grouped into families based on the type of sugar they transfer (galactosyltransferases, sialyltransferases, fucosyltransferases, acetylgalactosaminyltransferases). As used herein the abbreviation GT refers to UDP-D-galactose:N-acetylglucosamine β-1,4-galactosyltransferase; ST refers to CMP-N-acetylneuraminate:Galβ1,3(4)GlcNAc α-2,3-sialyltransferase; FTVII refers to GDP-L-fucose:(β-D-galactosyl)-N-acetylglucosamine-3-α-1-fucosyltransferase VII; and GNT refers to UDPGalNAc:β-1,4acetylgalactosaminyltransferase.

cDNAs have been obtained for many glycosyltransferases. Table 1 ((Paulson, J. C. and K. J. Colley, J. Biol. Chem. 264(30):17615–17618, 1989) shows six glycosyltransferases for which cDNAs have been obtained.

TABLE 1

Cloned glycosyltransferases involved in the synthesis of terminal sequences in sugar chains of glycoproteins and glycolipids

| Glycosyltransferase | Donor Substrate | Sequence Formed |
|---|---|---|
| Galactosyltransferases | | |
| GlcNAcβ1,4-GT (E.C. 2.4.1.38) | UDP-Gal | Galβ1,4GlcNAc-R |
| Galα1,3-GT (E.C. 2.4.1.151) | UDP-Gal | Galα1,3Galβ1,4GlcNAc-R |
| Sialyltransferase Galα2,6-ST (E.C. 2.4.99.1) | CMP-NeuAc | NeuAcα2,6Galβ1,4GlcNAc-R |
| Fucosyltransferases | | |
| GlcNAcα1,3-FT (E.c. 2.4.1.65) | GDP-Fuc | 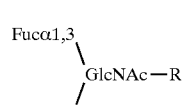 |

TABLE 1-continued

Cloned glycosyltransferases involved in the synthesis of terminal sequences in sugar chains of glycoproteins and glycolipids

| Glycosyltransferase | Donor Substrate | Sequence Formed |
|---|---|---|
| | | 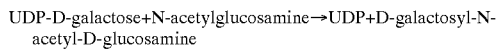 |
| Galα1,2-FT (E.C. 2.4.1.69) | GDP-Fuc | Fucα1,2Galβ1,4GlcNAc-R Fucα1,2Galβ1,3GalNAc-R |
| N-Acetylgalactosaminyltransferase Galα1,3-GalNAcT (Blood group A transferase) | UDP-GalNAc | 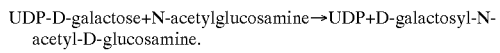 |

Abbreviated names combine the acceptor sugar, the linkage formed, and the glycosyltransferase family (GT, galactosyltransferase; ST, sialyltransferase; FT, fucosyltransferase; Gal NacT, N-acetylgalactosaminyltransferase). For the sequence formed, the sugar transferred is highlighted in boldface, and the acceptor sequence is shown in lightface. R represents the remainder of the glycoprotein or glycolipid sugar chain.

Galactosyltransferase (GT)

Most tissues of vertebrates contain the enzyme galactosyltransferase, which promotes the transfer of a D-galactose residue to N-acetylglucosamine in the reaction:

UDP-D-galactose+N-acetylglucosamine→UDP+D-galactosyl-N-acetyl-D-glucosamine

This reaction is a step in the biosynthesis of the carbohydrate portion of glycoproteins and glycolipids which contain galactose. A species of galactosyltransferase which catalyzes this reaction is UDP-D-galacctose:N-acetylglucosamine β-1,4-galactosyltransferase.

Polynucleotides

Polynucleotides employed in the invention for recombinantly modifying NSO-like cells include DNA, cDNA and RNA sequences which encode galactosyltransferase (GT) and, in particular, UDP-D-galacctose:N-acetylglucosamine β-1,4-galactosyltransferase or portions thereof which catalyze the reaction:

UDP-D-galactose+N-acetylglucosamine→UDP+D-galactosyl-N-acetyl-D-glucosamine.

Sources of polynucleotides encoding, respectively, GT, ST, FTVII, and GNT are set forth in Example 1, below.

It is understood that all polynucleotides encoding all or a portion of GT are also included herein, as long as they encode a polypeptide with an activity that catalyzes the reaction UDP-D-galactose+N-acetylglucosamine→UDP+D-galactosyl-N-acetyl-D-glucosamine. Such polynucleotides include naturally occurring, synthetic, and intentionally manipulated polynucleotides. For example, GT polynucleotide may be subjected to site-directed mutagenesis. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of GT polypeptide encoded by the nucleotide sequence is functionally, i.e. catalytically unchanged.

Minor modifications of the GT primary amino acid sequence may result in proteins which have substantially equivalent activity as compared to the GT described herein. Such proteins include those defined by the term "having essentially the amino acid sequence" of the galactosyltransferase encoded by the polynucleotide contained in plbGT-1. All of the polypeptides produced by these modifications are included herein as long as the biological activity of GT exists, namely catalyzing the reaction:

UDP-D-galactose+N-acetylglucosamine→UDP+D-galactosyl-N-acetyl-D-glucosamine.

Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GT enzymatic activity.

The polynucleotide sequence encoding the GT polypeptide includes, but is not restricted to, the sequences available in cDNAs (Masri, et al., *Biochem Biophys Res Commun*, 157:657–663, 1988; D'Agostaro, et al., *Eur J Biochem*, 183:211–217, 1989; Russo, et al., *J Biol Chem*, 265:3324–3331, 1990; Nakazawa, et al., *J Biochem*, 104:165–168, 1988; and Shaper, et al., *J Biol Chem*, 263:10420–10428, 1988) and genomic DNAs (Shaper, et al., *Somat Cell Mol Genet*, 12:633–636, 1986; Shaper, et al., *Cytogenet Cell Genet*, 44:18–21, 1987; and Hollis, et al., *Biochem Biophys Res Commun*, 162(3):1069–1075, 1989) and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that the substituted polypeptide retains the biological catalytic activity of the unsubstituted polypeptide.

Sources of Glycosyltransferase Polynucleotides. Any polynucleotide or nucleic acid specimen, in purified or nonpurified form, can be utilized as the starting nucleic acid or acids, provided it contains, or is suspected of containing, the specific nucleic acid sequence containing the polynucleotide encoding a glycosyltransferase, or, in particular, GT. Thus, the invention may employ, for example, DNA or RNA, including messenger RNA, wherein DNA or RNA may be single-stranded or double-stranded.

DNA Sequences. DNA sequences which encode GT and are useful in the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the GT polynucleotide encoding the enzyme produced by the gene expression system and method of the invention is derived from a mammal. A preferred GT polynucleotide is from a bovine source, such as clone plbGT-1 (Naramatsu et al, *Proc. Nat. Acad. Sci. USA* 83:4720–4724, 1986). However, other sources of polynucleotide useful in the invention for producing GT are available, and include, but are not restricted to the sequences available in cDNAs (Masri, et al., *Biochem Biophys Res Commun*, 157:657–663, 1988; D'Agostaro, et al., *Eur J Biochem*, 183:211–217, 1989; Russo, et al., *J Biol Chem*, 265:3324–3331, 1990; Nakazawa, et al., *J Biochem*, 104:165–168, 1988; and Shaper, et al., *J Biol Chem*, 263:10420–10428, 1988) and genomic DNAs (Shaper, et al., *Somat Cell Mol Genet*, 12:633–636, 1986; Shaper, et al, *Cytogenet Cell Genet*, 44:18–21, 1987; and Hollis, et al., *Biochem Biophys Res Commun*, 162(3):1069–1075, 1989).

Other sources of GT polynucleotide can be obtained using screening procedures which rely on nucleic acid hybridization that make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981; Maniatis, et al., *Molecular Cloning: A Laboratory Manual*, Cold Spring Harbor, N.Y. 1989).

The development of specific DNA sequences encoding GT can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

The synthesis of DNA sequences is frequently the method of choice when the entire sequence of amino acid residues of the desired polypeptide product is known. The entire nucleotide and acid and amino sequences of GT are known (Naramatsu et al, *Proc. Nat. Acad. Sci. USA* 83:4720–4724, 1986). When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

Polynucleotides useful in the invention preferably have an operative linkage with a leader sequence. Leader sequences which find use in the invention include preproalbumin, pre-IgG light chain, prelysozyme, preprolactin, prepenicillinase (*E. coli*), prevesicular stomatitis virus (VSV) glycoprotein, and prelipoprotein (*E. coli*), D. P. Leader, *TIBS*, 4:205, 1979. A preferred leader sequence is the human preproinsulin leader. FIG. 1A–D and SEQ ID NOs. 1–8 illustrate operative linkages between the human preproinsulin leader and the stem region of either GT, ST, FTVII or GNT. These sequences were expressed as fusion proteins.

Techniques for construction and expression of fusion proteins are well known in the art (Current Protocols in Molecular Biology, Chapters 9 (II) and 16.4, eds. Ausubel, F. et al., 1994). The term "operative linkage" refers to the organization of the nucleotide sequence such that the regulatory elements and the coding sequences are in functional linkage. The term "isolated" refers to a polynucleotide substantially free of other polynucleotides, proteins, lipids, carbohydrates or other materials with which it is naturally associated.

Specifically disclosed herein is a gene expression system recombinantly modified with a DNA sequence containing the stem region of the bovine GT gene. The sequence contains an open reading frame (ORF) of approximately 1000 base pairs which are transcribed into GT product having a biological activity that catalyzes the reaction: UDP-D-galactose+N-acetylglucosamine→UDP+D-galactosyl-N-acetyl-D-glucosamine.

Expression. Polynucleotide sequences encoding GT can be expressed by polynucleotide transfer into a suitable host cell. It was anticipated that polynucleotide sequences encoding, respectively, GT, ST, FTVII, and GNT would, after transfer into host cells, express at approximately the same levels. However, it was unexpectedly found that GT polynucletide sequences encoding GT expressed substantially more gene product than did the polynucleotide sequences encoding either ST, FTVII, or GNT.

"Host cells" are cells in which a vector can be propagated and its DNA expressed. A gene expression system is comprised of a host cell in which a vector was propagated and the vector's DNA expressed. The term "host cell" also includes any progeny of the subject host cell. It is understood that all progeny may not be identical to the parental cell since there may be mutations that occur during replication. However, such progeny are included when the term "host cell" is used. Host cells which are useful in the claimed gene expression system and the claimed method of producing galactosyltransferase include myeloma cells having the characteristics of NSO cells. Most preferred is the NSO cell designated ECACC No. 8511503, in which it was unexpectedly found (See "Results" in Examples below) that DNA sequences encoding GT overproduced gene product compared to the production of gene product encoded, respectively, by DNA sequences for either ST, FTVII or GNT.

Methods of stable transfer, meaning that the foreign DNA is continuously maintained in the host, are known in the art. In the present invention, the GT polynucleotide sequences may be inserted into a recombinant expression vector. The term "recombinant expression vector" refers to a plasmid, virus or other vehicle known in the art that has been manipulated by insertion or incorporation of the GT genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Such methods of transfection of DNA using calcium phosphate co-precipitates, conventional mechanical procedures such as microinjection, electroporation, insertion of a plasmid encased in liposomes, or virus vectors may be used. Host cells can also be transformed with DNA sequences which not only encode GT, but, preferably also code for a selectable marker encoding a selectable phenotype. A preferred selectable marker in NSO-like cells is the glutamine synthetase (GS) gene. NSO-like cells cannot grow on glutamine-free medium because they lack a functional gene encoding GS, which is required for glutamine synthesis. As described in the Examples below, methionine sulphoximine (MSX) is an inhibitor of glutamine synthetase, which binds irreversibly to GS and renders it inactive. MSX is toxic to NSO cells and to NSO cells transfected with a plasmid (e.g. pEE12 plasmid) encoding GS and linked with a polynucleotide sequence encoding GT. NSO cells transfected with GS cDNA attempt to overcome MSX toxicity by amplifying GscDNA sequences to produce more GS. MSX binds to the GS enzyme. A sufficient amount of amplification of GS sequences, with concommitant amplification of linked GT sequence, produces more GS enzyme to "dilute out" the effect of MSX, which allows some NSO cells to live in selective (i.e. glutamine-free) medium. Thus MSX resistance enhances GT expresion in NSO cells. MSX resistance enhances GT-expression in NSO cells.

Host cells can also be contransformed with DNA sequences encoding GT and a second foreign DNA molecule encoding a selectable phenotype, such as the herpes simplex thymidine kinase gene. Another method is to use a eukaryotic viral vector, such as simian virus 40 (SV40) or bovine papilloma virus, to infect or transform eukaryotic cells and express the protein. (see for example, *Eukaryotic Viral Vectors*, Cold Spring Harbor Laboratory, Gluzman ed., 1982).

GT polypeptides, in particular, UDP-D-galacctose:N-acetylglucosamine β-1,4-galactosyltransferase, are produced by the claimed gene expression system, which comprises a myeloma cell having the characteristics of an NSO cell recombinanatly modified with a polynucleotide encoding galactosyltransferase which catalyzes the reaction:

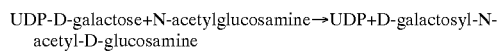
UDP-D-galactose+N-acetylglucosamine→UDP+D-galactosyl-N-acetyl-D-glucosamine The method of the invention produces GT polypeptides which are substantially pure. As used herein, the term "substantially pure" refers to a protein which is free of other proteins, lipids, carbohydrates or other materials with which it is naturally associated. One skilled in the art can purify GT polypeptides using standard techniques for protein purification including preparative chromatography and immunological separations involving monoclonal or polyclonal antibodies. For example, the substantially pure GT will yield a single major band of approximately 45 kD on a non-reducing polyacrylamide gel. The purity of the GT polypeptides can also be determined by amino-terminal amino acid sequence analysis. GT polypeptides include functional fragments of the polypeptide, as long as the activity of remains. Accordingly, the invention includes a gene expression system and a method of producing GT which produce smaller peptides containing the biological activity of GT.

Cell Lines and Culturing

As used herein, the term "NSO" or "NSO-like" refers to cells which are derived from myeloma cells, are highly transfectable, and do not grow in gluatmine-free selection media. The murine myeloma line NSO is available from the European Collection of Animal Cell Cultures, having accesion no. 8511503 (Galfre and Milstein, *Methods in Enzymology* 73(B), 3–46 (1981)).

Deposited Cell Line. The following recombinantly modified NSO cell line, identified herein as NSO-GT-12 (also called GT-59 Amp-12 herein) was deposited on Mar. 19, 1996, with the American Type Culture Collection, 1301 Parklawn Drive, Rockville, Md., U.S.A. 20852(ATCC):

| Deposit | ATCC Accession No. |
| --- | --- |
| NSO-GT-12 | ATCC CRL12066 |

This cell line or gene expression system under non-stress culture conditions produces high levels of galactosyltransferase, in particular, UDP-D-galacctose:N-acetylglucosamine β-1,4-galactosyltransferase, which catalyzes the reaction:

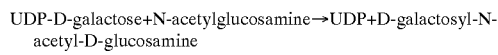
UDP-D-galactose+N-acetylglucosamine→UDP+D-galactosyl-N-acetyl-D-glucosamine This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The cells will be made available by ATCC under the terms of the Budapest Treaty and Applicant assures permanent and unrestricted availability of the progeny of the culture to the public upon issuance of the pertinent U.S.

patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR § 1.14 with particular reference to 886 OG 638). The assignee of the present application has agreed that if the culture deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

As set forth in detail below, all NSO cells were cultured in media formulated for either cell maintenance (non-selective media), selection, amplification, or production. For production of GT from the recombinantly modified cell of the invention, any liquid medium which supports growth, proliferation, and expression of the polynucleotide sequence encoding galactosytransferase can be used in the invention. One such medium, as described below in Example 2, was an IMDM selection medium supplemented with 0.1% F68 (Pluronic F68, Sigma #P1300). A preferred medium for production was a supplemented custom formulation of Hybridoma/SFM (Gibco/BRL #94-0365SA), also described below in Example 2. Another medium useful for production of GT from the gene expression system and method of the invention is IMDM selective medium require (Example 2). Such media are well known in the art.

Production of GT. Production of GT from the gene expression system of the invention is achieved by culturing a gene expression system comprising a myeloma cell having the characteristics of an NSO cell recombinantly modified with a polynucleotide encoding galactosyltransferase, in particular, UDP-D-galacctose:N-acetylglucosamine β-1,4-galactosyltransferase, or an enzymatically active portion thereof which catalyzes the reaction:

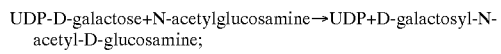

UDP-D-galactose+N-acetylglucosamine→UDP+D-galactosyl-N-acetyl-D-glucosamine;

and harvesting the galactosyltransferase. The method further comprises substantially purifying the harvested galactosyltransferase using protein purification protocols well known in the art (*Current Protocols in Molecular Biology*, Chapter 10, eds. Ausubel, F. M. et al., 1994).

The method for producing GT involves culturing the gene expression system of the invention under conditions of continous culture, such as, but not restricted to, "fed-batch cultures" or continuous perfusion cultures, as described in Example 5, below. Continuous culture conditions in the method of the invention achieves advantages over cell-stress production methods. These advantages are: (a) production of the GT enzyme without substantial proteolytic damage and contamination from cell death, (b) operation of the culture system for longer periods than cell stress enzyme production systems, allowing continuous harvest of enzyme, and [c] upon harvesting, does not require extra labor and material for reinoculating into fresh media in sterile vessels in order to eliminate proteolytic enzymes and other contaminants.

Other continuous culture systems which find use in the present invention is set forth in Wang, G. et al. *Cytotecnology* 9:41–49, 1992; Kadouri, A. et al. *Advances in Animal Cell Biology and Technology for Bioprocesses*, pp. 327–330, Courier International, Ltd., 1989; Spier, R. E. et al. *Biotechnol. Bioeng.* 18:649–57, 1976.

The following examples are intended to illustrate but not limit the invention. While they are typical, other procedures known to those skilled in the art may alternatively be used to illustrate the embodiments and methods of the invention.

EXAMPLE 1

Source of Polynucleotides Encoding GT, ST, FTVII, and GNT

Source of GT Clone

A partial cDNA clone of bovine GT DNA as described in Narimatsu et al. *Proc. Natl. Acad. Natl. Sci. USA* 83:4720–4724 (1986) was obtained from Dr. Pradman Qasba at the National Institutes of Health. This clone, called pLbGT-1, lacks the amino-terminal transmembrane region and begins within the stem region. To generate a secreted enzyme, the stem region was fused in frame to the human insulin leader sequence (FIG. 1A and SEQ ID NOs. 1 and 2). Other leader sequences known in the art are useful for fusion with the stem region to generate a secreted enzyme are illustrated in Table 2. Plasmid pLbGT-1 was digested with the enzymes Sst I and EcoRI (New England Biolabs) using conditions provided by the manufacturer and fractionated on an agarose gel. The 1.4 kb fragment was isolated using Qiaex matrix (Qiagen) and ligated under standard conditions into the SstI (5'-end) and EcoRI(3-end') sites of plasmid pGIR199, generating pGIR199-GT.

Source of ST Clone

This clone is described in Wen et al. *J. Biol. Chem.* 267:21011–21019 (1992). A recombinant chimeric cDNA clone encoding a secreted form of ST cloned (rat cDNA) into the BamHI (5'-end) and EcoRI (3'-end) sites of plasmid pGIR199 was made and obtained from the authors. The sequence of the fused DNA construct is shown in FIG. 1B and SEQ ID NOs. 3 and 4. Plasmid pGIR199 (Huseh et al. *J. Biol. Chem.* 261:4940 (1986)) is a derivative of pSP64 (Promega; Madison, Wis.) and contains an NheI restriction enzyme recognition site 5' to the site of the chimeric signal/ST DNA insertion. A clone was chosen and designated pNSTL.

Source of FTVII Clone

Plasmid pGIR199-FTVII, as described in Natsuka et al. *J. Biol. Chem.* 269: 16789–16794 (1994) was obtained from Dr. John Lowe at the University of Michigan. Briefly, the plasmid pCDM8-FTVII, which contains the human FTVII gene was digested with the enzymes Kpn I and Sph I (New England Biolabs) using conditions provide by the manufacturer and fractionated on an agarose gel. The 1.1 kb fragment was isolated and sequentially treated with Klenow (to fill in the Sph I site; New England Biolabs) and T4 DNA polymerase (to blunt the Kpn I site; New England Biolabs) and then cloned into the Klenow-blunted Xba I site of PGIR199, using conditions provided by the manufacturer, generating plasmid pGIR199-FTVII. This plasmid contains the FTVII gene fused in frame to the human preproinsulin leader sequence (FIG. 1C and SEQ ID NOs. 5 and 6). The FTVII gene in this construct lacks the amino terminal transmembrane domain and thus produces a secreted protein.

Source of GNT Clone

Plasmid PCDM8-GNT, construction of which is described in Smith and Lowe *J. Biol. Chem.* 269: 15162–15171 (1994), was obtained from Dr. John Lowe at the University of Michigan. This plasmid contains the GNT gene fused in frame to the human preproinsulin leader sequence (FIG. 1D and SEQ ID NOs. 7 and 8). The GNT gene in this construct lacks the transmembrane domain and thus produces a secreted protein.

Construction of pEE12-Glycosyltransferase Plasmids

The expression vector pEE12 (see FIG. 2) was obtained from Celltech Limited (Slough Berkshire, England). This plasmid contains a cDNA encoding the hamster glutamine synthetase (GS) under the control of the SV40 Early promoter and SV40 splicing and polyadenylation signals, obtained from pSV2.GS (see Bebbington, C. R. and Hentschel, C. C., *DNA Cloning* Vol. III, D. Glover (Ed.), IRL Press, 163–188(1987)).

Downstream of the SV40-GS transcription unit is a human cytomegalovirus (HCMV) DNA sequence containing the complete enhancer, promoter and 5'-untranslated region from the major immediate early gene. This is followed by a multi-linker cloning site (see FIG. 2) and the SV40 Early-polyadenylation signal. The HCMV-SV40 expression cassette and bacterial plasmid sequences, containing a replication origin and an ampicillin resistance gene for maintenance in *E. coli,* were obtained from plasmid pEE6.hCMV (see Stephens and Cockett *Nucleic Acids Research,* 17:7110 (1989)).

Construction of pEE12-GT

The plasmid pGIR199-GT, was digested by the restriction endonuclease Nhe I (New England Biolabs) using conditions provided by the manufacturer and fractionated on an agarose gel. The 1.0 kb fragment was isolated and cloned into the Xba I restriction site of pEE12 following standard techniques generating the plasmid pEE12-GT.

Construction of pEE12-ST

The plasmid pNSTL was digested by the restriction endonuclease Nhe I using conditions provided by the manufacturer and fractionated on an agarose gel. The 2.0 kb fragment was isolated and cloned into the Xba I restriction site of pEE12 following standard techniques generating the plasmid pEE12-ST.

Construction of pEE12-FTVII

Plasmid pGIR199-FTVII was digested with restriction enzymes NheI and EcoRI (New England Biolabs) using conditions provided by the manufacturer and fractionated on an agarose gel. The 1.2 kb fragment was isolated and cloned into the XbaI (5'end) and Eco RI(3'-end) restriction sites of pEE12 following standard techniques generating the plasmid pEE12-FTVII.

Construction of pEE12-GNT

The GNT DNA was amplified from pCDM8-GNT by using native Pfu polymerase (Stratagene) and the polymerase chain reaction (PCR) using Buffer #1 and conditions supplied by the manufacturer. The primers generate an XbaI restriction site at the 5' terminus and a Bcl I site at the 3' terminus. The 5' primer was designed to hybridize to the stem portion of the GalNAcT gene, which fuses in frame to the human insulin leader sequence (FIG. 1D and SEQ ID NOs. 7 and 8). The 3' primer was designed to amplify the 3' end of the GNT coding region including the stop codon. The 5' and 3' primers were 5'-GC-TCT-AGA-CTT-ACA-ACA-GAC-TTC-3' and 5'-ATCTGA-TCA-TTG-CGA-TTC-CTG-GTC-TTG-3', respectively. The PCR procedure amplified the stem region and catalytic domain of the GalNAcT gene, yielding a 1.4 kb fragment. The amplified GNT gene was sequentially digested with the enzymes Bcl I (New England Biolabs) at 50° C. and XbaI at 37° C. The 1.4 kb fragment was fractionated on an agarose gel and isolated using standard techniques. Plasmid pEE12-GT was digested with the restriction endonucleases Xba I(5'end) and Bcl I(3'end) and the 8.1 kb fragment isolated. (The unique Xba I site originates from the polylinker sequence that is flanked by the human insulin leader and the GT cDNA sequences.) The 1.4 kb fragment was cloned into the 8.1 kb fragment following standard techniques generating pEE12-GNT.

EXAMPLE 2

Cell Line and Media

The murine myeloma line NSO was obtained from Celltech Limited (Slough Berkshire, England) (see Galfre and Milstein *Methods in Enzymology* 73(B), 3–46 (1981)); The murine myeloma line NSO is also available from the European Collection of Animal Cell Cultures, having accesion no. 8511503). NSO cells are highly transfectable and do not grow nor yield variants that grow in glutamine-free selection media. NSO was maintained in non-selective media: Iscove's Modification of DMEM (IMDM, Sigma, #I4136), supplemented with 10% heat inactivated fetal bovine serum (JRH Biosciences, #12-10378P) and 2 mM L-glutamine (Gibco/BRL #320-5030AG).

Selective medium consisted of a custom media formulation of DMEM, without glutamine, without ferric nitrate, supplemented with 110 mg/l sodium pyruvate and 4500 mg/l D-glucose (Gibco/BRL formula No. 93-0232AJ), which was supplemented with 10% heat inactivated dialyzed fetal bovine serum (JRH Biosciences#12-10578P), IX non-essential amino acids (NEAA, 100× stock, Gibco/BRL #320-1140PG), 60 mg/l asparagine (Sigma #A4159), 60 mg/l glutamate (Sigma #G5889), 7 mg/l adenosine (Sigma #A4036), 7 mg/l guanosine (Sigma #G6264), 7 mg/l cytidine (Sigma #C4654), 7 mg/l uridine (Sigma #U3003), 2.4 mg/l thymidine (Sigma #T1895).

An alternate selective medium consisted of Iscove's Modified Eagles Medium (IMDM, Sigma I4136), supplemented with 10% heat inactivated dialyzed fetal bovine serum, 60 mg/l asparagine, 60 mg/l glutamate, 7 mg/l adenosine, 7 mg/l guanosine, 7 mg/l cytidine, 7 mg/l uridine, 2.4 mg/l thymidine.

Amplification medium was prepared using the IMDM selective media, supplemented with L-methionine sulphoximine (MSX, Sigma #M5379) at final concentrations between 5 $\mu$M and 200 $\mu$M. (A 100 mM stock solution is made in phosphate buffered saline, filter sterilized and stored frozen at −20° C.)

Two production media were prepared. One was simply the IMDM selection medium described above supplemented with 0.1% F68 (Pluronic F68, Sigma #P1300). The second medium was a custom formulation of Hybridoma/SFM (Gibco/BRL #94-0365SA) supplemented with 0.5% dialyzed heat inactivated fetal calf serum (FCS), 0.1% F68, and 7 mg/l adenosine, 7 mg/l cytidine, 7 mg/l guanosine, 7 mg/l uridine, 240 $\mu$g/l thymidine, 75 mg/l glutamate, 75 mg/l asparagine, 13 mg/l aspartic acid (Sigma #A4534), 11.5 mg/l proline (Sigma #P4655), 9 mg/l alanine (Sigma #A4534 and 10 mg/l serine (Sigma #S5511).

EXAMPLE 3

Transformation of NSO Cells

PEE12 plasmids encoding any of the four glycosyltransferases were linearized (40 $\mu$g) with the restriction enzyme Sal I (New England Biolabs) using conditions provided by the manufacturer, ethanol precipitated, and resuspended in sterile 10 mM Tris, 1 mM EDTA, pH 8.0 at a final concentration of 1 $\mu$g/ml.

NSO cells were grown in non-selective medium to a density of 8×10$^5$ cells/ml with viability greater than 95%

(determined by trypan blue dye-exclusion). Cells ($10^7$) were pelleted in a clinical centrifuge and washed once with cold sterile phosphate buffered saline (PBS, Biowhittaker #17-516B) and then pelleted again. The pellet was resuspended in PBS (1 ml) and stored on ice.

Linearized DNA (40 µl) and the NSO cell suspension (0.8 ml) were aliquoted into an electroporation cuvette (0.4 mm gap, Biorad #165-2088) and incubated on ice for 5 minutes. A "Gene Pulser" electroporator (Biorad) was used to deliver two sequential pulses of 1500 volts, 3 µfarads to the DNA/cell suspension. The cuvette was then incubated on ice for five minutes.

The DNA/cell suspension was diluted in non-selective media to prepare three cell suspensions with cell densities at $2.67 \times 10^5$, $6.67 \times 10^4$, and $1.33 \times 10^4$ cells/ml, respectively. Using a multi-channel pipettor, cell suspensions were plated at 50 µl per well into 96-well flat bottom tissue culture plates (Falcon #3072) and incubated at 37° C. Selective media (150 µl per well) were added 24 hr later. The plates were incubated until substantial cell death had occurred and discrete surviving colonies appeared. This procedure allowed the cells to deplete the medium of residual glutamine so that the glutamine concentration declined gradually.

Resistant clones were isolated and plated into the wells of a 24-well cluster plate (Falcon #3047) and grown until the cells reached cell densities greater than $5 \times 10^5$ cells/ml and then the media was assayed for galactosyltransferase activity. Positive clones were then expanded in T-25 cm² flasks. For further analyses some producers were diluted to approximately $1-2 \times 10^5$ cells/ml selective media supplemented with 0.05–0.10% pluronic F68 (a surfactant to minimize mechanical damage, Sigma #P1300). Cell suspensions (8 ml) were aliquoted into sterile Erlenmeyer flasks (125 ml; Corning #25605) aseptically gassed with a 5% $CO_2$/95% air mixture and sealed. The flasks were placed in a Series 25 Incubator shaker (New Brunswick Scientific Company, Inc.) and shaken at 130 rpm at 37° C. for 7–9 days. Alternatively, cells were inoculated into 100 ml Spinner flasks (BELLCO Biotechnology, #1965-00100) at a 100 ml final volume, at a density of $1-2 \times 10^5$ cells/ml in selective media supplemented with 0.05–0.10% pluronic F68. The spinners were incubated (with side-arms loosened for gas exchange) for 7–8 days in a 37° C. humidified incubator (5% $CO_2$/95% air atmosphere) on a Cellgro Magnetic Stirrer (Model S45625, Thermolyne, Dubuque, Iowa) set at 60 rpm.

EXAMPLE 4

Selection for Vector Amplification and Clone Isolation

Independent transfected cell lines producing significant amounts of galactosyltransferase were expanded to masss culture for vector amplification. A cell suspension was prepared at a density of $4 \times 10^5$ cells/ml in selective media (IMDM base). The cells were distributed at 0.5 ml/well in a 24-well plate. One-half ml of selective medium containing MSX was added to each well to bring the final concentrations to 20, 40, 60, 80, 100, 140, or 180 µM. The plates were incubated at 37° C. for 3–4 weeks until descreet MSX-resistant colonies appeared. The pools were assayed for galactosyltransferase activity and expanded.

Single MSX-resistant clones were isolated by limiting dilution cloning. We found initially that simply plating serial dilutions of MSX resistant cells into 96-well plates did not produce single isolated clones—an appropriate feeder cell population was needed. A cell suspension of parental NSO cells was prepared in selective media supplemented with the appropriate concentration of MSX at a cell density of $10^5$ cells/ml and was aliquoted into a 96-well plate (at 0.1 ml/well. Serial 1:2 dilutions of MSX-resistant cell population (in MSX supplemented selective media) were plated (0.1 ml/well) into helper-cell containing 96-well plate. The parental NSO cells will die in the MSX-supplemented selective media but will provide sufficient media conditioning to allow MSX-resistant cell clones to grow.

Isolated clones were expanded (without helper cells) to wells of a 24-welll plate, then 25 cm² T-flasks, and were growth in 100-ml spinner flasks for 7 days or shaker flasks for 7 days as described above.

EXAMPLE 5

Large Scale Production of GT Enzyme

1. Fed-Batch Production

To produce 17-liter batches of GT from NSO cells a Wheaton Proteus 2000 Bioreactor was used following the instructions provided by the manufacturer (Wheaton Instruments, Millville, N.J., owners manual, rev. 0792) and using software provide by the manufacturer (Proteus Control Software, IBM/Compatible (3.0) Version, Ver. 7/92). A CellGas™ Oxygenator module (1.0 m², #CG2M-100-01N, Microgon Inc., Laguna Hills, Calif.) was used to allow continuous bubble-free control of bioreactor gas exchange. Gas exchanged occured across the hydrophobic hollow fiber membranes. Individual membrane fibers were free to move between fixed endcaps which were secured inside the bioreactor. Connected to the gas supply via a pipe through the head plate the spent gas was directed toward the headspace. The media used was either the selective medium IMDM base (10% FCS) or the Hybridoma/SFM (0.5% FCS) described above, both media were supplemented to 0.1% F68 to minimize shear damage.

Cells were grown to mass culture to a density between $6.0-10.0 \times 10^5$ cells/ml in 2-liter spinner flasks. Cells grown in the IMDM base (2–3 liters) were pelleted by centrifugation and resuspended in one-liter of fresh media and inoculated in 16-liters of fresh media. Cells grown in the Hybridoma-SFM base (2–3 liters) were directly inoculated into fresh media, bringing the final volume to 17 liters. In all cases the bioreactor was maintained with these parameters: 37° C., 70%-air dissolved oxygen, 7.0 pH, 60 rpm. When the cell density reached between $8-10 \times 10^5$ cells/ml 200 ml of MEM Amino Acid Solution (with L-glutamine, 50X, Gibco/BRL # 21135-025) was added. When the cell viability (determined by trypan blue staining) reached 40%, the run was terminated, the media clarified by centrifugation and prepared for GT-purification. A typical batch took 7–8 days from inoculation to termination.

2. Perfusion Production

Figure 3:
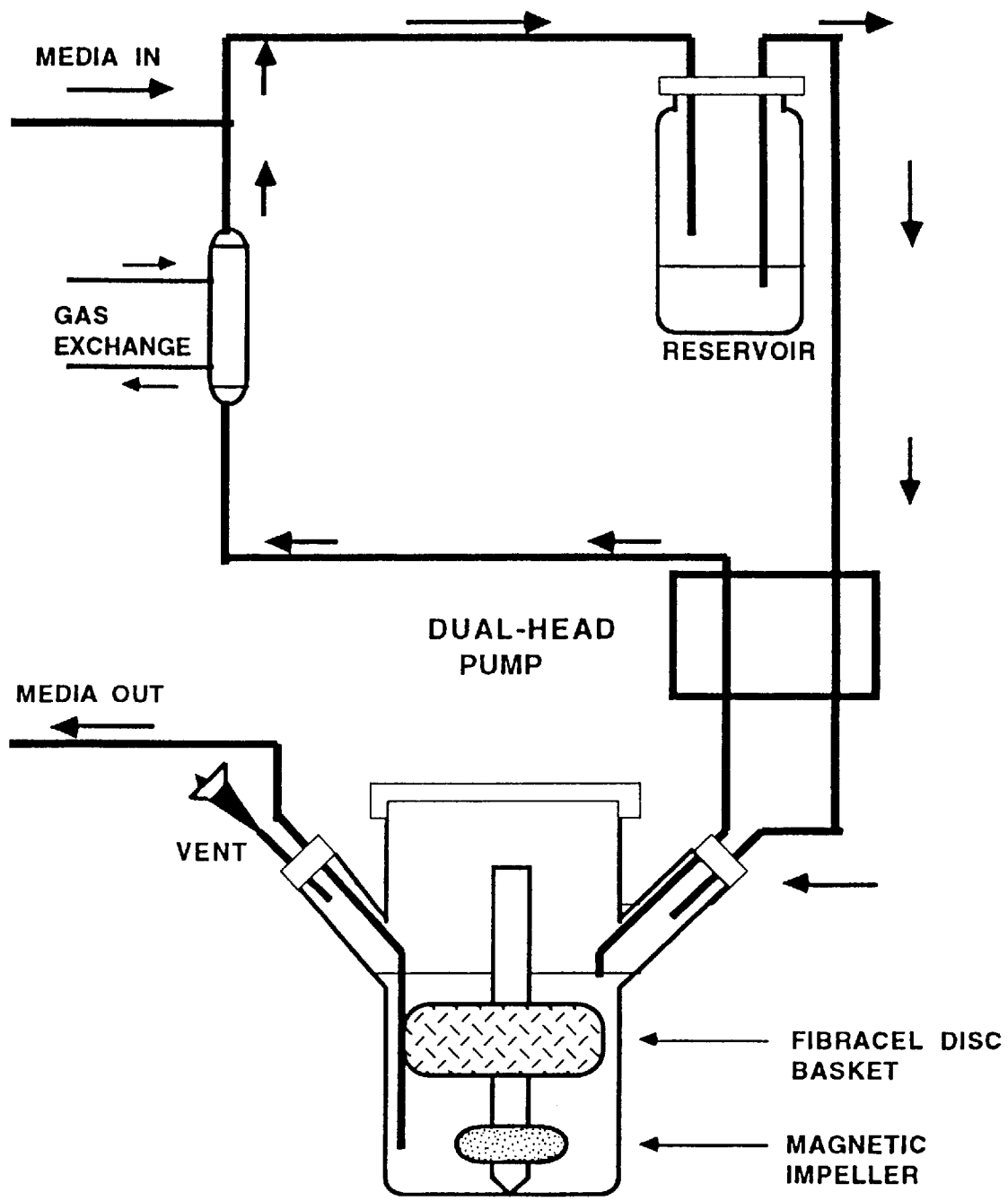
FIG. 3 is a schematic diagram of galactosyltransferase production under conditions of continuous culture.

Cells were grown in a Spinner Basket I Cell Culture Bioreactor (New Brunswick Scientific Co., Edison, N.J.) which consists of a glass jar with a working volume of 500 ml, a fixed bed with 10 grams non-woven polyester discs (M1176-9984) and a magnetic stirrer. The Spinner Basket 1 was prepared for inocculation following instructions provided by the manufacturer (Manual M1222-0050, Rev. A, released Mar. 29, 1993). Essentially 10 grams of the polyester discs were packed into the fixed bed, the spinner flask filled with phosphate buffered saline and autoclaved for 25 minutes at 121° C. After autoclaving, the Spinner Basket I was allowed to cool, the PBS was pumped out, and 500 ml fresh media pumped in and then pumped out twice to rinse the fixed bed of discs. 400 mL of fresh media was pumped into the flask then 100 mls of media containing cells at a density of $5 \times 10^5$ cells/mL. After the cells had become sequestered into the fixed bed (6 hrs), media circulation began, and the magnetic stirrer (Wheaton Micro-Spin,

902400, Wheaton Instruments) was turned on a rate of 100 rpm. The flask was connected to sterile C-Flex tubing (⅛" I.D.,# 6424-67, Cole-Parmer, Chicago, Ill.) using an SCD IIB automatic sterile tube welder (Terumo, Elkton, Md.) as diagrammed in FIG. 3. Media was circulated in a recirculation loop at 800 ml/hour using a dual-head peristaltic pump (Masterflex Model No. 7524-1, Cole-Parmer Instrument Co.). The media was passed through a Cell-Pharm™ Hollow Fiber Oxygenator (OXY-10, Unisyn Fibertec Corp., San Diego, Calif., #240-530) that was connected by a T-connector to an air tank, and a 10% $CO_2$/90% air tank. The flowrate was at 150 ml/min for air and between 1–10 ml/min for the $CO_2$. The $CO_2$ flow rate was determined empirically by observing the color of media and adjusting the flow rate so that the media appeared the same color pink (from the pH indicator) that media manifests at pH 7.0. Spent media was harvested from the sytem via a peristaltic at a rate of 400 ml–1000 ml/day, and fresh media was introduced via another peristaltic pump at the appropriate replenishment rate. The complete system was set up in a 37° C. room. Media that was used was the Hybridoma-SFM (0.5% FCS, no F68 supplementation) described above. The perfusion study ran for 3 weeks. Media harvests were measured for GT activity as described below.

EXAMPLE 6

Assay for Galactosyltransferase

1. GT Assay

This protocol was used to quantitate the GT expression in NSO cells. This assay measured the rate of transfer of $^3$H-galactose from UDP-[$^3$H]-galactose to N-acetylglucosamine, resulting in the formation of N-acetyllactosamine:

UDP-gal+GlcNAc→LacNAc+UDP

This neutral disaccharide product was then separated from the charged compound UDP-galactose by ion exchange on a Dowex 1-X8 column.

Preparation of 1X Reaction Mix

The reaction mixture was made fresh each day; the total amount prepared was determined by the number of samples. Each reaction mix (90 μl) contained: 1.0 μCi (5 μL of 250 μCi/2.5 ml) of uridine 5'diphospho-[$^3$H]-galactose (NEN#NET-213) solution, (evaporated using a stream of nitrogen in a 12×75 mm borosilicate glass tube); 0.63 mM uridine 5'diphosphogalactose (sodium salt, Sigma#U4500); 50 mM 3[N-Morpholino] propanesulfonic acid (sodium salt, Sigma #M9381), pH7.4; 30 mM $MnCl_2$ (Sigma#M3634); 0.2 mg/ml bovine serum albumin (Sigma#A6793); 20 mM N-acetyl-D-glucosamine (Sigma.#A8625). The assay mixture was stored on ice until use.

Resin Preparation 50 grams of AG 1-X8 Resin (100–200 mesh, chloride form, Biorad #140-1441) were swollen in 150 ml distilled $H_2O$ for 15 minutes. The resin was allowed to settle to the bottom and then excess $H_2O$ was decanted. This washing step was repeated three more times with 100 ml of distilled $H_2O$. The resin was resuspended with 100 ml distilled $H_2O$ to make a 50% slurry.

Column Preparation 1 ml of the 50% Dowex resin slurry was added to each Pasteur pipet plugged with glass wool. Once the resin had settled the resin was washed with 1 ml of distilled $H_2O$.

Assay Procedure

To each reaction mixture a 10 μl sample was added. The samples were diluted in 100 mM N-[2-Hydroxyethylpiperazine-N'-[2-ethanesulfonic acid] (Calbiochem.# 391338), 1% BSA, pH 7.4. The tubes were incubated at 37° C. in a heating block for a specific time interval. Reactions were terminated by removing the tubes from the heating block and immediately adding 1 ml of ice-cold distilled $H_2O$. Each reaction was loaded into Dowex column that was secured in a two-hole rubber stopper which in turn was placed on top of a scintillation vial. The eluate was collected in the vial. Each column was washed twice with 1 ml of distilled $H_2O$—each scintillation vial collected a total volume of 3 ml of eluate/washes.

Total available counts were determined by aliquoting 90μ of reaction mix and 3 mls of distilled $H_2O$ into a scintillation vial. 15 ml of scintillation cocktail (ScintiVerse BD, Fisher Sci. #SX18-4) were added to each vial.

A unit of GT activity is defined as the generation of 1 μmole of N-acetyllactosamine produced in one minute.

2. ST Assay

This protocol describes the procedure used to measure the enzymatic activity of ST preparations. This assay measures the rate of transfer of $^{14}$C-sialic acid from CMP-[$^{14}$C]-sialic acid to lacto-N-tetraose resulting in the formation of sialyl-lacto-N-tetraose and CMP:

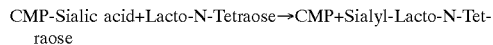

CMP-Sialic acid+Lacto-N-Tetraose→CMP+Sialyl-Lacto-N-Tetraose

The sialylated product is separated from the unsialylated material on a column of ion exchange resin (AG1X8, phosphate form).

Preparation of IX Reaction Mix

Each reaction mix (25 μL) contained: 0.02 μCi of cytidine-5'-monophosphate-[$^{14}$C]-sialic acid (NEN #NEC-619) solution (evaporated using a stream of nitrogen in a 12×75 mm borosilicate glass tube), 0.24 mM cytidine-5'-monophosphate-sialic acid (Boehringer Mannheim #1110306), 60 mM sodium cacodylate (Sigma #C0250), 0.6% Triton CF-54 (Sigma #CF-54), 0.9 mg/ml BSA (Sigma#A6793), 0.24 mM lacto-N-tetraose (Sigma #L6770), and 24 mM manganese chloride (Sigma #M3634), pH 6.5.

Resin Preparation 500 grams of AG1-X8 resin (200–400 mesh, chloride form, Bio Rad #140-1451) were swollen in 2.0 liters of 0.1M phosphoric acid for 15 minutes. The resin was allowed to settle to the bottom of the vessel and the excess liquid decanted. The washing step was repeated with 3-liter and 2-liter aliquots of distilled water, then a 2-liter aliquot of phosphate buffer saline (PBS, Bio Whittaker #17-516B), and then 3-liter and 2-liter aliquots of distilled water. The resin was resuspended with distilled water to make a 50% slurry.

Column Preparation 1 ml of the 50% Dowex resin slurry was added to each Pasteur pipet plugged with glass wool. Once the resin had settled the resin was washed with 1 ml of distilled water.

Assay Procedure

To each reaction mixture (25 μL) a 5 μl sample was added. The tubes were incubated at 37° C. in a heating block for a specific time interval (usually 15 minutes). Reactions were terminated by removing the tubes from the heating block and immediately adding 1 ml of ice-cold distilled water. Each reaction was loaded into a Dowex column that was secured in a two-hole rubber stopper which in turn was placed on top of a scintillation vial. The eluate was collected in the vial. Each column was washed twicd with 2 ml of distilled water—each scintillation vial collected a total volume of 3 ml of eluate/washes.

Total available counts were determined by aliquoting 25 μL of reaction mix and 3 mLs of distilled water into a scintillation vial. 15 mL of scintillation cocktail (ScintiVerse BD, Fisher Scientic #SX18-4) were added to each vial.

A unit of ST activity is defined as the generation of 1 µmole of sialyl-lacto-N-tetraose produced in one minute.

3. FTVII Assay

This assay was used to measure the enzymatic activity of the FTVII that catalyzes the following reaction:

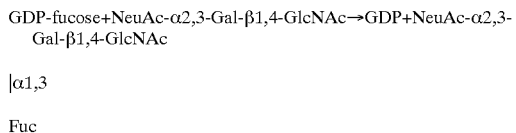

GDP-fucose+NeuAc-α2,3-Gal-β1,4-GlcNAc→GDP+NeuAc-α2,3-Gal-β1,4-GlcNAc

|α1,3

Fuc

The fucosylated product is separated from GDP-fucose on a column of ion exchange resin. Using the [$^{14}$C]-labelled substrate allows measurement of the fucosylated product by liquid scintillation counting.

Preparation of 1X Reaction Mix

The reaction mixture was made up fresh each day for the total number of reactions needed. Each reaction contained: 0.05 µCi of a guanosine diphosphate-[$^{14}$C(U)]-fucose (NEN #NEC-640) solution (evaporated with a nitrogen stream in a 12×75 mm borosilicate glass culture tube), 80 µM unlabeled GDP-fucose (Sigma #G4401), 50 mM sodium cacodylate, pH 6.0, 20 mM $MnCl_2$, and 20 mM α2,3-sialyl-N-acetyllactosamine,tetra (Cytel) in a final volume of 45 µl. The assay mixture was stored on ice until use.

Resin Preparation 50 grams of AG 1-X8 Resin (100–200 mesh, chloride form, Biorad #140-1441) were swollen in 150 ml distilled $H_2O$ for 15 minutes. The resin was allowed to settle to the bottom and then excess $H_2O$ was decanted. This washing step was repeated threemore times with 100 ml of distilled $H_2O$. The resin was resuspended with 100 ml distilled $H_2O$ to make a 50% slurry.

Column Preparation 1.5 mL of the 50% Dowex resin slurry was added to each Pasteur pipet plugged with glass wool. Once the resin had settled the resin was washed with 1 ml of distilled $H_2O$.

Assay Procedure

Each reaction mixture (45 µl) was preincubated at 37°. To each reaction tube 5 µl of sample was aliquoted. The tubes were incubated at 37° C. in a heating block for a specific time interval (usually 5–10 minutes). Reactions were terminated by removing the tubes from the heating block and immediately adding 1 mL of ice-cold distilled water. Each reaction was loaded into a Dowex column that was secured in a two-hole rubber stopper which in turn was placed on top of a scintillation vial. The eluate was collected in the vial. Each column was washed once with 1 ml of distilled water—each scintillation vial collected a total volume of 2 ml of eluate/washes. To each vial, aqueous scintillation fluid (15 ml; ScintiVerse BD, Fisher) was added, shaken vigorously, and counted in a liquid scintillation counter. A unit of FTVII activity is defined as the generation of 1 µmole of fucosylated product produced in one minute.

4. GNT Assay

This assay was used to measure the enzymatic activity of GNT that catalyzes the following reaction:

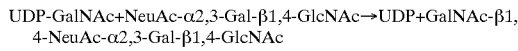

UDP-GalNAc+NeuAc-α2,3-Gal-β1,4-GlcNAc→UDP+GalNAc-β1,4-NeuAc-α2,3-Gal-β1,4-GlcNAc

The product is separated from UDP-GalNAc on a column of ion exchange resin.

Preparation of 1X Reaction Mix

The reaction mixture was made up fresh each day for the total number of reactions needed. Each reaction contained: 0.25 µCi of a uridine diphosphate-N-acetyl-D-galactosamine, [Galactosamine-1-$^3$H(N)] (NEN #NET-465) solution (evaporated with a nitrogen stream in a 12×75 mm borosilicate glass culture tube), 19.2 nmoles unlabeled UDP-GalNAc (Sigma #U5252), 50 mM HEPES, pH 7.4, 20 mM $MnCl_2$, and 20 mM α2,3-sialyl-N-acetyllactosaniline, tetra (Cytel) in a final volume of 45 µl. The assay mixture was stored on ice until use.

Resin Preparation 50 grams of AG 1-X8 Resin (100–200 mesh, chloride form, Biorad #140-1441) were swollen in 150 ml distilled $H_2O$ for 15 minutes. The resin was allowed to settle to the bottom and then excess $H_2O$ was decanted. This washing step was repeated three more times with 100 ml of distilled $H_2O$. The resin was resuspended with 100 ml distilled $H_2O$ to make a 50% slurry.

Column Preparation 1.5 mL of the 50% Dowex resin slurry was added to each Pasteur pipet plugged with glass wool. Once the resin had settled the resin was washed with 1 ml of distilled $H_2O$.

Assay Procedure

Each reaction mixture (45 µl) was preincubated at 37° for 5 min. To each reaction tube 5 µl of sample was aliquoted. The tubes were incubated at 37° C. in a heating block for a specific time interval (usually 5–10 minutes). Reactions were terminated by removing the tubes from the heating block and immediately adding 1 ml of ice-cold distilled water. Each reaction was loaded into a Dowex column that was secured in a two-hole rubber stopper which in turn was placed on top of a scintillation vial. The eluate was collected in the vial. Each column was washed once with 1 ml of distilled water—each scintillation vial collected a total volume of 2 ml of eluate/washes. To each vial, aqueous scintillation fluid (15 ml) was added, shaken vigorously, and counted in a liquid scintillation counter.

RESULTS

A. Transfected NSO Cells Express Soluble Galactosyltransferase

Table 2 summarizes the number of clones screened and the number of positive clones found from all four soluble glycosyltransferase cDNA's transfected into NSO cells. Table 2 also shows the accumulated galactosyltransferase activities from the best producer clone from each transfection (cells were grown in 100 ml spinner flasks for 7 days as described above). GT was expressed at very high levels (2,900 U/liter) compared to GNT (220 U/liter), ST (4 U/liter) and FTVII (3.4 U/liter). In view of an expectation that the GT, ST, FTVII and GNT genetic expression systems produced in these examples would all yield effective producers of the respective enzymes, it was surprising to find that the GT genetic expression sysem was substantially advantageous in yield compared to ST, FTVII, and GNT genetic expression systems.

Table 3 summarizes the results of expressing the same cDNA's in the baculovirus/*Spodoptera frugiperda* (Sf9) system and the *Aspergillus niger* system following state-of-the-art procedures.

B. MSX Resistance Enhances GT-expression in NSO Cells

Table 4 shows the accumulated GT-activity of the six best GT-producer clones grown in shaker flasks for 7 days. Clones GT-46, GT-51, and GT-59 were grown to mass culture and plated in selective media supplemented with methionine sulfoximine (MSX) in the range of 20 µM to 180 µM as described above. In all cases colonies arose at the 20 µM MSX supplemented media. Clone GT-59 generated 7 clones with an average activity of 1600 U/liter; clone GT-46 generated 4 clones with an average activity of 500 U/liter; and clone GT-51 generated 4 colonies with an average activity of 30 U/liter. Colonies generated from GT-46 and GT-51 were discarded. Two of the colonies generated from GT-59—clones GSGT59-3 and GSGT59-4—were pooled and grown to mass culture to inoculate in a Proteus 2000 bioreactor and plated with NSO helper cells to isolate single colonies by limiting dilution cloning described above.

Table 5 shows the accumlated activity from 7-day growth in shaker flasks for the four best amplified clones. The parental clone, GT-59, produced 2,300 U/liter GT under the same conditions that the four clones GT-59Amp-3, GT-59Amp-12, GT-59Amp-46, and GT-59Amp-62 produced 3,365–4,190 U/liter. These four clones were all grown in Hybridoma-SFM media 10% FCS, 20 $\mu$M MSX, and were serially passaged to lower concentrations of FCS. Only clone GT-59Amp-12 maintained its GT production in Hybridoma-SFM supplemented with 0.5% FCS, 20 $\mu$M MSX.

C. GT Can Be Expressed at High Levels by Fed-batch Culture

Table 6 shows the results of 9 different runs of NSO-59Amp cells grown in a 20-liter Wheaton Proteus 2000 bioreactor. The first batch was run with a pool of clones GSGT59-3 and GSGT59-4, the second through fourth batches were inoculated with clone GT-59Amp-62, and the remaining five batches were inocculated with clone GT-59Amp-12. The last five batches used media that was supplemented with 0.5% fetal bovine serum—lowering the serum concentration lowers production costs and increases purification yield.

D. GT Can Be Generated through Perfusion Technology

Clone GT-59Amp-12 was inoculated ($5 \times 10^7$ total cells) in a Spinner Basket I as described above. The cells became sequestered into the 100 ml fixed bed of polyester discs ($5 \times 10^5$ cells/ml disc). After 2.5 weeks, the cells reached a density of $2.5 \times 10^7$ cells/ml disc, which is 25% of theoretical yield. At this density the bioreactor produced an average of 1,000 U/day for four days.

This pilot study demonstrated that these cells could be grown in Hybridoma-SFM, 0.5% FCS and in perfusion mode. It was not possible to monitor and correct changes in dissolved oxygen, pH, glucose consumption, and lactate production on a real-time basis.

Use of a New Brunswick Celligen Plus™ Bioreactor (New Jersey) that can accommodate fixed-beds of 0.7, 1.5, and 2.5 liters which, if an increase of at least two-fold in cell density by optimizing culture parameters were assumed, would extrapolate to a product of GT of 14,000, 30,000, and 50,000 U/day, respectively.

TABLE 2

Results of NSO cells transfected with cDNAs Encoding different glycosyltransferases and Maximum accumulated activity from best Initial producers.

| Enzyme | Number Positive | Number Screened | Percent Positive | Accumulated units/liter from Spinner |
| --- | --- | --- | --- | --- |
| GT | 23 | 66 | 34.9 | 2,300.0 |
| ST | 18 | 186 | 9.7 | 4.0 |
| FTVII | 14 | 35 | 40.0 | 3.4 |

TABLE 2-continued

Results of NSO cells transfected with cDNAs Encoding different glycosyltransferases and Maximum accumulated activity from best Initial producers.

| Enzyme | Number Positive | Number Screened | Percent Positive | Accumulated units/liter from Spinner |
| --- | --- | --- | --- | --- |
| GNT | 5 | 12 | 41.7 | 220.0 |

TABLE 3

Comparison of GT and ST cDNA expression in different Expression systems

| Expression System | ST (units/liter) | GT (units/liter) |
| --- | --- | --- |
| NSO/GS | 4 | 2,300 |
| Baculovirus/Sf9 | 140 | 350 |
| *Aspergillus niger* | 1,700 | 5 |

TABLE 4

Accumulated GT Activity from NSO Cultures Grown for Seven Days in Shaker Flasks.

| NSO-GT Clone | GT Activity (Units/L) |
| --- | --- |
| GT-5 | 719 |
| GT-28 | 686 |
| GT-46 | 1,365 |
| GT-51 | 1,368 |
| GT-54 | 611 |
| GT-59 | 2,856 |

TABLE 5

Accumulated GT Activity from Isolated 20 $\mu$M MSX Resistant NSO Cultures Grown for Seven Days in Shaker Flasks.

| Amplified GT Clone | Accumulated Units/Liter |
| --- | --- |
| GT-59Amp-3 | 4,041 |
| GT-59Amp-12 | 4,106 |
| GT-59Amp-46 | 3,365 |
| GT-59Amp-62 | 4,190 |

TABLE 6

Results of GT Fed-Batch Runs in a Wheaton PROTEUS 2000 (17-Liter Batches)

| Cells | Media | Concen. (Units/L) | Total Units |
| --- | --- | --- | --- |
| GT-59Amp-Pool | IMDM/10% FCS | 3,720 | 63,240 |
| GT-59Amp-62 | IMDM/10% FCS | 4,214 | 71,640 |
| GT-59Amp-62 | IMDM/10% FCS | 4,482 | 76,190 |
| GT-59Amp-62 | IMDM/10% FCS | 4,765 | 81,000 |
| GT-59Amp-12 | HYB-SFM/0.5% FCS | 7,500 | 127,500 |
| GT-59Amp-12 | HYB-SFM/0.5% FCS | 4,400 | 74,800 |
| GT-59Amp-12 | HYB-SFM/0.5% FCS | 4,600 | 78,200 |
| GT-59Amp-12 | HYB-SFM/0.5% FCS | 3,721 | 63,000 |

What is claimed is:

1. A method for producing galactosyltransferase, comprising the steps of:
   (a) culturing a gene expression system comprising the HSO cell having the accession number ATCC No. CRL 12066 which is recombinantly modified with a polynucleotide encoding the galactosyltransferase or an enzymatically active portion thereof which catalyzes the reaction:

UDP-D-galactose+N-acetylglucosamine→UDP+D-galactosyl-N-acetyl-D-glucosamine;

and (b) harvesting the galactosyltransferase.

2. A recombinantly modified NSO cell having the accession no. ATCC No. CRL 12066.

* * * * *